United States Patent [19]

Habener

[11] Patent Number: 5,118,666
[45] Date of Patent: Jun. 2, 1992

[54] INSULINOTROPIC HORMONE

[75] Inventor: Joel F. Habener, Newton, Mass.

[73] Assignee: The General Hospital Corporation, Charlestown, Mass.

[21] Appl. No.: 532,111

[22] Filed: Jun. 1, 1990

Related U.S. Application Data

[63] Continuation of Ser. No. 148,517, Jan. 26, 1988, abandoned, which is a continuation-in-part of Ser. No. 859,928, May 5, 1986, abandoned.

[51] Int. Cl.$^5$ .............. A61K 37/02; A61K 37/28; C07K 7/10; C07K 7/34
[52] U.S. Cl. .................................. 514/12; 514/866; 530/308; 530/324
[58] Field of Search .............. 530/324, 303, 308; 514/12, 866

[56] References Cited

FOREIGN PATENT DOCUMENTS 0044168 1/1982 European Pat. Off. .

OTHER PUBLICATIONS

Uttenthal et al., J. Clin. End. Metab. 61=472-479 (1985).
Ghiglione et al., Diabetologia, 27=599-600 (1984).
Rudinger, Peptide Hormones, Parsons (Ed.) U. Park Press, Baltimore, pp. 1-7 (1976).
Schmidt et al., Diabetologia 28=704-707 (1985).
Bell et al., Nature, 302=716-718 (1983).
Andrews et al., J. Biol. Chem. 260=3910-3914.
Houghten, R. A. et al., Biotechniques 4:522-524, 526, 528 (Jul. 1986).
Meienhofer, J., In: Peptides 1984, Ragnarsson, U. (ed.) Almqvist & Wiksell International, Stockholm (1984).
Sarson, D. L. et al., Diabetologia 22:33 (1982).
Hauner, H. et al., Ann. Nutr. Metab. 32:282-288 (1989).
Ganong, W., Review of Medical Physiology, 9th Ed., Lange Medical Publications, Los Altos, CA (1979) pp. 257-276.
Drucker, D. J. et al., Proc. Natl. Acad. Sci. USA 84:3434-3438 (1987).
Mojsov, S. et al., J. Clin. Invest. 79:616-619 (1987).
Holst, J. J. et al., FEBS Lett. 211:169-174 (1987).
Kreymann, B. et al., The Lancet, Dec. 5, 1987, pp. 1300-1304.
Weir, G. et al., Diabetes 38(3):338-342 (Mar. 1989).
Gefel, D. et al., Endocrinology 126 (4):2164-2168 (1990).

Primary Examiner—John Doll
Assistant Examiner—Christina Chan
Attorney, Agent, or Firm—Sterne, Kessler, Goldstein & Fox

[57] ABSTRACT

Derivatives of glucagon-like peptide I (GLP-1) have been found to have insulinotropic activity. The invention pertains to such derivatives, and to the use of such derivatives as a potential therapy for Diabetes Mellitus.

21 Claims, 6 Drawing Sheets

```
                                                                         135 GLP II                                    145
His Ala Asp Gly Ser Phe Ser Asp Glu Met Asn Thr Ile Leu Asp Asn Leu Ala Thr Arg
CAT GCT GAT GGA TCC TTC TCT GAT GAG ATG AAC ACG ATT CTC GAT AAC CTT GCC ACC AGA    555
                                     E-5
                    155
Asp Phe Ile Asn Trp Leu Ile Gln Thr Lys Ile Thr Asp (Lys) (Lys) End
GAC TTC ATC AAC TGG CTG ATT CAA ACC AAG ATC ACT GAC  AAG   AAA  TAG gaatatttccattt   618
                              E-6
cacaaccatcttcacaacatctcctgccagtcactggatgtacattgagagcatatccgaagctatactgctttgc       697 atgcggacgaatacatttccctttagcgttgtgtaacccaaaggttgtaaatgaataaagttttccagggtgttgat     776 aaagtaacaactttacagtatgaaaatgctggattctcaaattgtctcctcgttttgaagttaccgccctgagattact   855 tttctgtggtataaattgtaaattatcgcagtcacgacacctggattacaacaacagaagacatggtaacctggtaacc   933 gtagtggtgaacctggaaagagaacttctccttgaacccctttgtcataaatgcgctcagcttttcaatgtatcaagaat 1012 agatttaaataaatatctcat                                                           1024
3'
```

*FIG. 1 CONT.*

INSULINOTROPIC HORMONE

CROSS-REFERENCE TO RELATED APPLICATIONS

This application is a continuation of application Ser. No. 07/148,517, filed Jan. 26, 1988, now abandoned, which is a continuation-in-part of U.S. patent application Ser. No. 859,928, filed on May 5, 1986, and now abandoned.

BACKGROUND OF THE INVENTION

1. Field of the Invention

This invention is directed to the discovery that certain peptide fragments of the prehormone, proglucagon, possess hormonal activities and can be used to stimulate the synthesis and secretion of the hormone, insulin. These peptide fragments are useful in therapy for the disease Diabetes mellitus.

2. Description of the Background Art

The endocrine secretions of the pancreatic islets are under complex control not only by blood-borne metabolites (glucose, amino acids, catecholamines, etc.), but also by local paracrine influences. The major pancreatic islet hormones (glucagon, insulin, and somatostatin) interact among their specific cell types (A, B, and D cells, respectively) to modulate secretory responses mediated by the metabolites. Although insulin secretion is predominantly controlled by blood levels of glucose, glucagon and somatostatin stimulate and inhibit glucose-mediated insulin secretory responses, respectively. In addition to the proposed interislet paracrine regulation of insulin secretion, there is evidence to support the existence of insulinotropic factors in the intestine. This concept originates from the observations that glucose taken orally is a much more potent stimulant of insulin secretion than is a comparable amount of glucose given intravenously.

The human hormone, glucagon, is a 29-amino acid peptide hormone produced in the A-cells of the pancreas. The hormone belongs to a multi-gene family of structurally related peptides that include secretin, gastric inhibitory peptide, vasoactive intestinal peptide, and glicentin. These peptides variously regulate carbohydrate metabolism, gastrointestinal mobility, and secretory processing. The principal recognized actions of pancreatic glucagon, however, are to promote glycogenolysis and gluconeogenesis, resulting in an elevation of blood sugar levels. In this regard, the actions of glucagon are counterregulatory to those of insulin and may contribute to the hyperglycemia that accompanies *Diabetes mellitus* (Lund, P. K., et al., *Proc. Natl. Acad. Sci., USA* 79:345-349 (1982)).

Glucagon has been found to be capable of binding to specific receptors which lie on the surface of insulin-producing cells. Glucagon, when bound to these receptors, stimulates the rapid synthesis of cAMP, by these cells. cAMP, in turn, has been found to stimulate insulin expression (Korman, L. Y., et al., *Diabetes* 34:717-722 (1985)). Insulin acts to inhibit glucagon synthesis (*Review of Medical Physiology*, Ganong, W. F., 1979, Lang Publications, Los Altos, California (p. 273)). Thus, the expression of glucagon is carefully regulated by insulin, and ultimately by the serum glucose level.

The glucagon gene is initially translated from a 630-base pair precursor to form the polypeptide, preproglycagon (Lund et al. (1982)). This polypeptide is subsequently processed to form proglucagon. Patzelt, C., et al. (*Nature* 282:260-266 (1979) demonstrated that proglucagon was subsequently cleaved into glucagon and a second polypeptide. Subsequent work by Lund, P. K., et al. (*Proc. Natl. Acad. Sci. USA* 79:345-349 (1982)); Lopez, L. C., et al. (*Proc. Natl. Acad. Sci. USA* 80:5485-5489 (1983)) and Bell, G. I., et al. (*Nature* 302:716-718 (1983)) demonstrated that the proglucagon molecule was cleaved immediately after lysine-arginine dipeptide residues. Studies of proglucagon produced by channel catfish (*Ictalurus punctata*) indicated that glucagon from this animal was also proteolytically cleaved after adjacent lysine-arginine and arginine-arginine dipeptide residues (Andrews, P. C., et al., *J. Biol. Chem.* 260:3910-3914 (1985)). Lopez, L. C., et al. (*Proc. Natl. Acad. Sci. USA* 80:5485-5489 (1983)), and Bell, G. I., et al., discovered the mammalian proglucagon was cleaved adjacent lysine-arginine or arginine-arginine dipeptides and demonstrated that the proglucagon molecule contained three discrete and highly homologous peptide molecules which were designated glucagon, glucagon-like protein 1 (GLP-1), and glucagon-like protein 2 (GLP-2). Lopez et al. concluded that glucagon-like protein 1 was 37 amino acid residues long and that glucagon-like peptide 2 was 34 amino acid residues long. Analogous studies on the structure of rat preproglucagon revealed a similar pattern of proteolytic cleavage between adjacent lysine-arginine or arginine-arginine dipeptide residues, resulting in the formation of glucagon, GLP-1, and GLP-2 (Heinrich, G., et al., *Endocrinol.* 115:2176-2181 (1984)). Human rat, bovine, and hamster sequences of GLP-1 have been found to be identical (Ghiglione, M., et al., *Diabetoloqia* 27:599-600 (1984)).

The conclusion reached by Lopez et al. (*Proc. Natl. Acad. Sci. USA* 80:5485-5489 (1983)) regarding the size of GLP-1 was confirmed by the work of Uttenthal, L. O., et al., (*J. Clin. Endocrinol. Metabol.* 61:472-479 (1985)). Uttenthal et al. examined the molecular forms of GLP-1 which were present in the human pancreas. Their research shows that GLP-1 and GLP-2 are present in the pancreas as proteins having 37 and 34 amino acid residues, respectively.

The similarity between GLP-1 and glucagon suggested to early investigators that GLP-1 might have biological activity. Although some investigators found that GLP-1 could induce rat brain cells to synthesize cAMP (Hoosein, N. M., et al., *FEBS Lett.* 178:83-86 (1984)), other investigators failed to identify any physiological role for GLP-1 (Lopez, L. C., et al., *Proc. Natl. Acad. Sci. USA* 80:5485-5489 (1983)). The failure to identify any physiological role for GLP-1 caused some investigators to question whether GLP-1 was in fact a hormone and whether the relatedness between glucagon and GLP-1 might be artifactual (Ghiglione, M., et al., *Diabetologia* 27:599-600 (1984)).

Thus, in conclusion, the prior art reveals an awareness of the processing of a glucagon hormone precursor into a set of peptides sharing extensive homology. It has been widely assumed by those of skill in the art that these highly related glucagon-like peptides would have a biological activity. Nevertheless, extensive investigations designed to elucidate the biological effects of these molecules had been unsuccessful.

SUMMARY OF THE INVENTION

The present invention relates to an insulinotropic hormone comprising GLP-1 and its derivatives. The invention additionally pertains to the therapeutic uses of such compounds.

In detail, the invention pertains to a peptide fragment which is insulinotropic and is derivable from a naturally occurring amino acid sequence.

The invention comprises a compound selected from the group consisting of:

(A) a peptide comprising the sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X
wherein X is selected from the group consisting of:
(a) Lys,
(b) Lys-Gly,
(c) Lys-Gly-Arg;
and (B) a derivative of the peptide; wherein the compound is substantially free of natural contaminants, and has an insulinotropic activity which exceeds the insulinotropic activity of GLP-1 (1-36) or GLP-1 (1-37).

The invention also includes a compound selected from the group consisting of:

(A) a peptide comprising the sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X
wherein X is selected from the group consisting of:
(a) Lys,
(b) Lys-Gly,
(c) Lys-Gly-Arg;
and (B) a derivative of the peptide; wherein the compound is substantially free of natural contaminants, and has an insulinotropic activity at a concentration of at least $10^{-10}$M.

Of particular interest are peptides of the following formula:

(1) $H_2N-X-CO-R^1$ wherein $R^1$ is OH, OM, or $-NR^2R^3$;

M is a pharmaceutically acceptable cation or a lower branched or unbranched alkyl group;

$R^2$ and $R^3$ are the same or different and selected from the group consisting of hydrogen and a lower branched or unbranched alkyl group;

X is a peptide comprising the sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg $NH_2$ is the amine group of the amino terminus of X; and CO is the carbonyl group of the carboxy terminus of X;

(2) the acid addition salts thereof; and (3) the protected or partially protected derivatives thereof;
wherein said compound has an insulinotropic activity which exceeds the insulinotropic activity of GLP-1 (1-36) or GLP-1 (1-37).

The invention further pertains to a method for enhancing the expression of insulin which comprises providing to a mammalian pancreatic B-type islet cell an effective amount of the insulinotropic peptides disclosed above.

DESCRIPTION OF THE PREFERRED EMBODIMENTS

A. GLP-1 and Its Derivatives

The hormone glucagon is known to be synthesized as a high molecular weight precursor molecule which is subsequently proteolytically cleaved into three peptides: glucagon, glucagon-like peptide 1 (GLP-1), and glucagon-like peptide 2 (GLP-2). GLP-1 has 37 amino acids in its unprocessed form. The present invention discloses that the unprocessed GLP-1 is essentially unable to mediate the induction of insulin biosynthesis. The unprocessed GLP-1 peptide is, however, naturally converted to a 31-amino acid long peptide (7-37 peptide) having amino acids 7-37 of GLP-1 ("GLP-1 (7-37)"). This processing occurs in the pancreas and the intestine. The 7-37 peptide which has not been previously described is a hormone that has insulinotropic activity. A compound is said to have an "insulinotropic activity" if it is able to stimulate, or cause the stimulation of, the synthesis or expression of the hormone insulin. The hormonal activity of GLP-1 (7-37) appears to be specific for the pancreatic beta cells where it appears to induce the biosynthesis of insulin. The insulinotropic hormone is useful in the study of the pathogenesis of maturity onset diabetes mellitus, a condition in which the dynamics of insulin secretion are abnormal. Moreover, the insulinotropic hormone is useful in therapy for this disease.

Peptide moieties (fragments) chosen from the determined amino acid sequence of human GLP-1 constitute the starting point in the development comprising the present invention. The interchangeable terms "peptide fragment" and "peptide moiety" are meant to include both synthetic and naturally occurring amino acid sequences derivable from a naturally occurring amino acid sequence.

Figure 1:
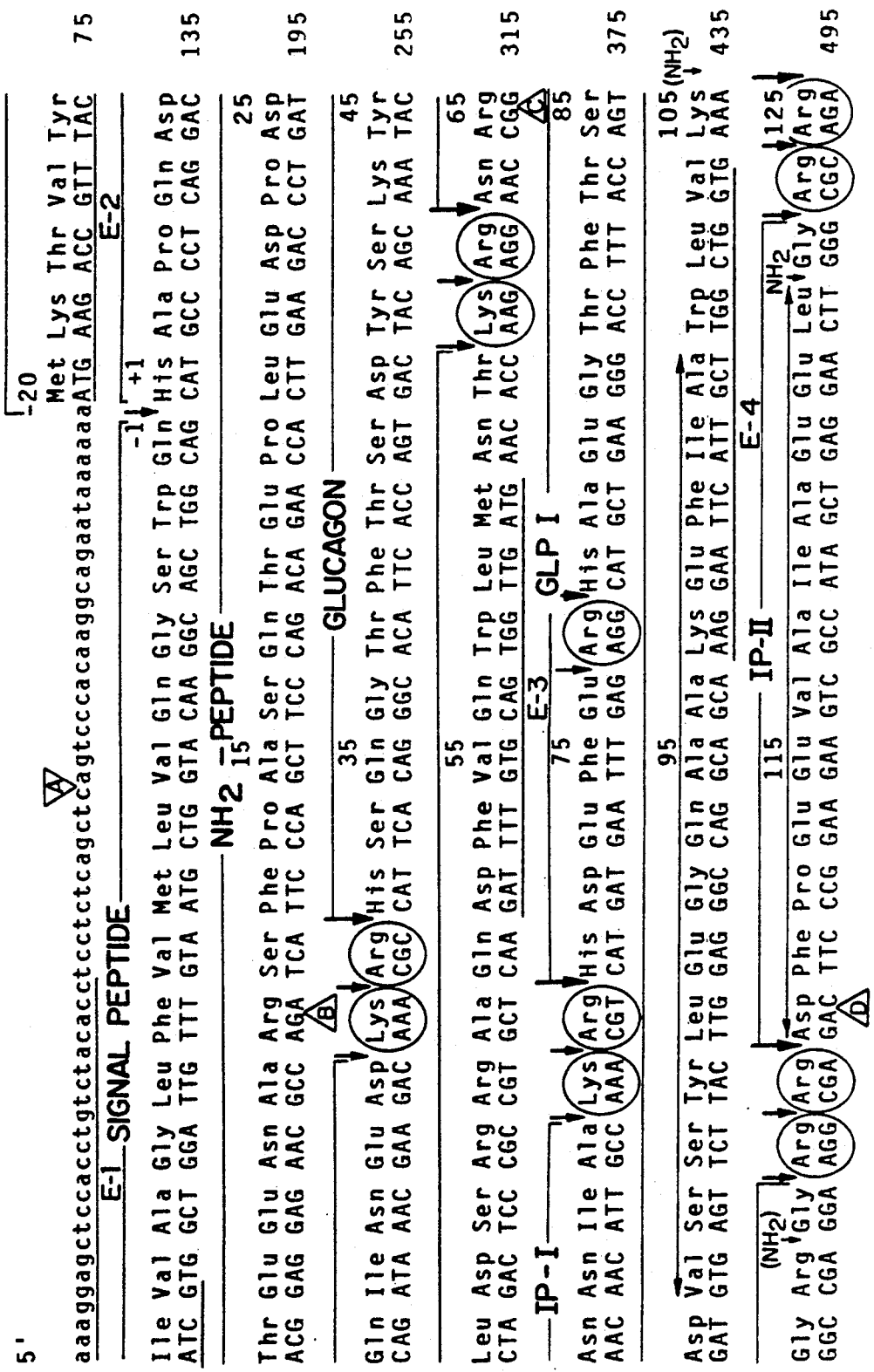
FIG. 1 shows the DNA structure and corresponding amino acid sequence of human, rat, and hamster preproglucagons. The preproglucagon precursor is proteolytically cleaved at sites indicated by circles.

The amino acid sequence for GLP-1 has been reported by several researchers (Lopez, L. C., et al., Proc. Natl. Acad. Sci., USA 80:5485– 5489 (1983); Bell, G. I., et a., Nature 302:716-718 (1983); Heinrich, G., et al., Endocrinol. 115:2176-2181 (1984); Ghiglione, M., et al., Diabetologia 27:599-600 (1984)). The structure of the preproglucagon gene and its corresponding amino acid sequence is shown in FIG. 1. This figure further displays the proteolytic processing of the precursor gene product into glucagon and the two glucagon-like peptides. As used herein, the notation of GLP-1 (1-37) refers to a GLP-1 polypeptide having all amino acids from 1 (N-terminus) through 37 (C-terminus). Similarly, GLP-1 (7-37) refers to a GLP-1 polypeptide having all amino acids from 7 (N-terminus) through 37 (C-terminus).

In one embodiment, GLP-1 (7-37) and its peptide fragments are synthesized by conventional means, such as by the well-know solid-phase peptide synthesis described by Merrifield, J. M. (*Chem. Soc.* 85:2149 (1962)), and Stewart and Young (*Solid Phase Peptide Synthesis* (Freeman, San Francisco, 1969), pages 27-66), which are incorporated by reference herein. However, it is also possible to obtain fragments of the proglucagon polypeptide, or of GLP-1, by fragmenting the naturally occurring amino acid sequence, using, for example, a proteolytic enzyme. Further, it is possible to obtain the desired fragments of the proglucagon peptide or of GLP-1 through the use of recombinant DNA technology, as disclosed by Maniatis, T., *et al., Molecular Biology: A Laboratory Manual,* Cold Spring Harbor, N.Y. (1982), which is hereby incorporated by reference.

The present invention includes peptides which are derivable from GLP-1 (1-37). A peptide is said to be "derivable from a naturally occurring amino acid sequence" if it can be obtained by fragmenting a naturally occurring sequence, or if it can be synthesized based upon a knowledge of the sequence of the naturally occurring amino acid sequence or of the genetic material (DNA or RNA) which encodes this sequence.

Included within the scope of the present invention are those molecules which are said to be "derivatives" of GLP-1 (1-37). Such a "derivative" has the following characteristics: (1) it shares substantial homology with GLP-1 (1-37) or a similarly sized fragment of GLP-1 (1-37); (2) it is capable of functioning as an insulinotropic hormone and (3) using at least one of the assays provided herein, the derivative has either (i) an insulinotropic activity which exceeds the insulinotropic activity of either GLP-1 (1-37) or GLP-1 (1-36), or, more preferably, (ii) an insulinotropic activity which can be detected even when the derivative is present at a concentration of $10^{-10}M$, or, most preferably, (iii) an insulinotropic activity which can be detected even when the derivative is present at a concentration of $10^{-11}M$.

A derivative of GLP-1 (1-37) is said to share "substantial homology" with GLP-1 (1-37) if the amino acid sequences of the derivative is at least 80%, and more preferably at least 90%, and most preferably at least 95%, the same as that of either GLP-1 (1-37) or a fragment of GLP-1 (1-37) having the same number of amino acid residues as the derivative.

The derivatives of the present invention include GLP-1 (1-37) fragments which, in addition to containing a sequence that is substantially homologous to that of a naturally occurring GLP-1 (1-37) peptide may contain one or more additional amino acids at their amino and/or their carboxy termini. Thus, the invention pertains to polypeptide fragments of GLP-1 (1-37) that may contain one or more amino acids that may not be present in a naturally occurring GLP-1 (1-37) sequence provided that such polypeptides have an insulinotropic activity which exceeds that of GLP-1 (1-37) or GLP-1 (1-36).

Similarly, the invention includes GLP-1 (1-37) fragments which, although containing a sequence that is substantially homologous to that of a naturally occurring GLP-1 (1-37) peptide may lack one or more additional amino acids at their amino and/or their carboxy termini that are naturally found on a GLP-1 (1-37) peptide. Thus, the invention pertains to polypeptide fragments of GLP-1 (1-37) that may lack one or more amino acids that are normally present in a naturally occurring GLP-1 (1-37) sequence provided that such polypeptides have an insulinotropic activity which exceeds that of GLP-1 (1-37) or GLP-1 (1-36).

The invention also encompasses the obvious or trivial variants of the above-described fragments which have inconsequential amino acid substitutions (and thus have amino acid sequences which differ from that of the natural sequence) provided that such variants have an insulinotropic activity which is substantially identical to that of the above-described GLP-1 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Examples of derivatives of GLP-1 (1-37) include GLP-1 (7-37); GLP-1 (7-36); GLP-1 (7-35); GLP-1 (7-34); and the des-Gly amidated forms of these molecules. Included as well are the use of additional amino acid residues added to such sequences in order to enhance coupling to carrier protein or amino acid residues added to enhance the insulinotropic effect.

As is known in the art, the amino acid residues may be in their protected or unprotected form, using appropriate amino or carboxyl protecting groups. Useful cations are alkali or alkaline earth metallic cations (i.e., Na, K, Li, 1/2Ca, 1/2Ba, etc.) or amine cations (i.e., tetraalkylammonium, trialkylammonium, where alkyl can be $C_1$–$C_{12}$).

The variable length peptides may be in the form of the free amines (on the N-terminus), or acid-addition salts thereof. Common acid addition salts are hydrohalic acid salts, i.e., HBr, HI, or, more preferably, HCl.

B. Assays of Insulinotropic Activity

The present invention concerns GLP-1 (1-37) derivatives which have an insulinotropic activity that exceeds the insulinotropic activity of either GLP-1 (1-37) or GLP-1 (1-36). The insulinotropic property of a compound may be determined by providing that compound to animal cells, or injecting that compound into animals and monitoring the release of immunoreactive insulin (IRI) into the media or circulatory system of the animal, respectively. The presence of IRI is detected through the use of a radioimmunoassay which can specifically detect insulin. Although any radioimmunoassay capable of detecting the presence of IRI may be employed, it is preferable to use a modification of the assay method of Albano, J. D. M., *et al., (Acta Endocrinol.* 70:487-509 (1972)). In this modification, a phosphate/-albumin buffer with a pH of 7.4 was employed. The incubation was prepared with the consecutive condition of 500 μl of phosphate buffer, 50 μl of perfusate sample or rat insulin standard in perfusate, 100 μl of anti-insulin antiserum (Wellcome Laboratories; 1:40,000 dilution), and 100 μl of insulin, giving a total volume of 750 μl in a 10×75-mm disposable glass tube. After incubation for 2-3 days at 4° C., free insulin was separated from antibody-bound insulin by charcoal separation. The assay sensitivity was 1-2 μU/ml. In order to measure the release of IRI into the cell culture medium of cells grown in tissue culture, one preferably incorporates radioactive label into proinsulin. Although any radioactive label capable of labeling a polypeptide can be used, it is preferable to use $^3H$ leucine in order to obtain labeling proinsulin. Labeling can be done for any period of time sufficient to permit the formation of a detectably labeled pool of proinsulin molecules; however, it is preferable to incubate cells in the presence of radioactive label for a 60-minute time period. Although any cell line capable of expressing insulin can be used for determining whether a compound has an insulinotropic effect, it is preferable to use rat insulinoma cells, and especially RIN-38 rat insulinoma cells. Such cells can be grown in any suitable medium; however, it is preferable to use DME medium containing 0.1% BSA and 25 mM glucose.

The insulinotropic property of a compound may also be determined by pancreatic infusion. The in situ isolated perfused rat pancreas preparation was a modification of the method of Penhos, J. C., et al. (*Diabetes* 18:733–738 (1969)). In accordance with such a method, fasted rats (preferably male Charles River strain albino rats), weighing 350–600 g, are anesthetized with an intraperitoneal injection of Amytal Sodium (Eli Lilly and Co., 160 ng/kg). Renal, adrenal, gastric, and lower colonic blood vessels are ligated. The entire intestine is resected except for about four cm of duodenum and the descending colon and rectum. Therefore, only a small part of the intestine is perfused, thus minimizing possible interference by enteric substances with glucagon-like immunoreactivity. The perfusate is preferably a modified Krebs-Ringer bicarbonate buffer with 4% dextran T70 and 0.2% bovine serum albumin (fraction V), and is preferably bubbled with 95% $O_2$ and 5% $CO_2$. A nonpulsatile flow, four-channel roller-bearing pump (Buchler polystatic, Buchler Instruments Division, Nuclear-Chicago Corp.) is preferably used, and a switch from one perfusate source to another is preferably accomplished by switching a three-way stopcock. The manner in which perfusion is performed, modified, and analyzed preferably follows the methods of Weir, G. C., et al., (*J. Clin. Investigat.* 54:1403–1412 (1974)), which are hereby incorporated by reference.

C. Formulations of Insulinotropic Compounds

The insulinotropic peptides (or peptide derivatives) of GLP-1 (1-37) may be used as therapeutic compositions. Such therapeutic compositions may consist solely of the insulinotropic peptides (or peptide derivatives) although, preferably, the compositions will contain the insulinotropic peptides (or derivatives thereof) combined in admixture with a pharmaceutically acceptable carrier vehicle.

Suitable vehicles and their formulation, inclusive of other human proteins, e.g., human serum albumin, are described for example in *Remington's Pharmaceutical Sciences* (16th Ed., A. Oslo Ed. Mack, Easton, Pa. (1980)). In order to form a pharmaceutically acceptable composition suitable for effective administration, such compositions will contain an effective amount of GLP-1 (7-37), or a derivative of GLP-1 (7-37), together with a suitable amount of carrier vehicle. The GLP-1 derivatives of such compounds will preferably have been purified so as to be substantially free of natural contaminants. A material is said to be "substantially free of natural contaminants" if it has been substantially purified from materials with which it is normally and naturally found. Examples of natural contaminants with which GLP-1 (7-37) might be associated are: other peptides, carbohydrates, glycosylated peptides, lipids, membranes, etc. A material is also said to be substantially free of natural contaminants if these contaminants are substantially absent from a sample of the material.

Compositions containing GLP-1 (7-37) or its derivatives may be administered intravenously, intramuscularly, or subcutaneously at dosages in the range of from about 1 pg/kg to 1,000 μg/kg body weight, or at concentrations sufficient to produce serum levels of $10^{-10}$M to $10^{-11}$M, although a lower or higher dosage may be administered. The required dosage will depend upon the severity of the condition of the patient and upon such criteria as the patient's height, weight, sex, age, and medical history.

For the purpose of parenteral administration, compositions containing the derivatives of GLP-1 (1-37) are preferably dissolved in distilled water and the pH-value is preferably adjusted to about 6 to 8. In order to facilitate the lyophilization process resulting in a suitable product, lactose may be added to the solution. Preferably, the solution is then filtered sterilized, introduced into vials, and lyophilized. The concentration of the GLP-1 (1-37) derivatives in these compositions may vary from to $10^{-12}$M to $10^{-5}$M.

Additional pharmaceutical methods may be employed to control the duration of action. Controlled release preparations may be achieved by the use of polymers to complex or adsorb the GLP-1 (1-37) derivatives. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the derivatives of GLP-1 (1-37) into particles of a polymeric material such as polyesters, polyamino acids, hydrogels, poly (lactic acid) or ethylene vinylacetate copolymers. Alternatively, instead of incorporating the GLP-1 (1-37) derivatives into these polymeric particles, it is possible to entrap these derivatives in microcapsules prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences* (1980).

It is possible to enhance the biological half-life of the GLP-1 (1-37) derivatives of the present invention, and, thus, to increase the retention or stability of the derivatives in a recipient, by bonding such derivatives to one or more chemical "moieties" to thereby produce a compound which can be recognized and processed within a recipient to yield a GLP-1 (1-37) derivative. The "moieties" of such compounds may include one or more lipids, carbohydrates, amino acid residues, etc. A preferred "moiety" is an amino acid residue. The most preferred "moiety" is a peptide. The amino terminal (histidine) residue of GLP-1 (7-37) is a preferred site for the bonding of the "moiety".

An appreciation of this aspect of the present invention can be obtained through a consideration of the natural processing of GLP-1 (1-37). GLP-1 (1-37) has a biological half-life of 30–50 minutes. A natural cleavage of the amino terminal hexapeptide, GLP-1 (1-6), occurs to yield GLP-1 (7-37) whose biological half-life is only 3–5 minutes. Thus, the amino terminal hexapeptide, GLP-1 (1-6) is a natural "moiety" which when bonded to GLP-1 (7-37) increases the biological half-life of GLP-1 (7-37). The discovery of such a natural "moiety" is disclosed in FIG. 5, and supports the concept that additional or alternative moieties may be employed in the same manner as GLP-1 (1-6) to increase the biological half-life of the GLP-1 (1-37) derivatives of the present invention. Although the present invention does not encompass the use of GLP-1 (1-6) as a "moiety," it does include variants of GLP-1 (1-6) as well as other peptides of unrelated sequence which are capable of enhancing the half-life of the peptides and peptide derivatives of the present invention.

In summary, insulin secretion from the $\beta$-cell of the endocrine pancreas is controlled by a complex network of metabolic factors. This network includes such diverse components as glucose, amino acids, catecholamines, and peptides. The decoding of the glucagon gene has uncovered two additional glucagon-like peptides encoded in proglucagon, the polypeptide precursor of glucagon. One of these peptides, glucagon-like peptide-1 (GLP-1) is processed from proglucagon in two forms: 37-amino acids GLP-1 (1-37) and 31-amino acid GLP-1 (7-37). The specific liberation of GLP-1 peptide's in the intestine and, to some degree, in the pancreas, suggested to the inventors that the GLP-1 peptide's might be components of the enteroinsular axis. To resolve this issue, the effects of the GLP-1 peptide's on a $\beta$-cell line was studied using a rat perfused pancreas and a cultured rat insulinoma cell-line. These studies have revealed that, in the isolated perfused pancreas, GLP-1 (7-37) is a potent stimulator of insulin secretion at concentrations as low as $5 \times 10^{-12}$M. Insulin release in response to GLP-1 (7-37) is highly dependent upon ambient glucose concentration. The longer peptide (GLP-1 (1-37)) has no insulin-releasing activity even at concentrations as high as $\times 10^{-7}$M. Comparison of the insulinotropic effects of GLP-1 (7-37) and glucagon showed that (in the rat perfused pancreas) GLP-1 (7-37) is at least 100 fold more potent in the stimulation of insulin sectretion. In the rat insulinoma cell line (RIN 1046-38) GLP-1 (7-37), at concentrations of $10^{-10}$M to $10^{-11}$M, increased both the cellular levels of cAMP (5-fold) and the levels of insulin mRNA (3-fold) and also stimulated insulin release. Again the effects of GLP-1 (7-37) were more potent than those of glucagon. The magnitude of the insulinotropic effects at such low concentrations renders GLP-1 (7-37) one of the most potent insulin secretagogues described, including glucagon and gastric inhibitory polypeptide. These results suggest that GLP-1 (7-37) may participate in the physiological regulation of $\beta$-cell functions.

Having now fully described the invention, the same will be more readily understood by reference to specific examples which are provided by way of illustration, and are not intented to be limiting of the invention, unless specified.

SPECIFIC EXAMPLES

EXAMPLE 1

Specificity of GLP-1 Peptides

In order to demonstrate that the effects of GLP-1 (1-37), GLP-1 (1-36) and GLP-1 (7-37) were specific for insulin, and were not capable of inducing or provoking non-specific gene expression, the effect of these peptides on the levels of insulin, actin and angioten-sinogen mRNAs in rat insulinoma cells were conducted.

Rat insulinoma cells of cell line RIN-38 were derived from a continuous islet cell line, RIN-r, which was established from a transplantable rat islet cell tumor (Gazdar, A. F., et al., Proc. Natl. Acad. Sci., USA 77:3519-3523 (1980)). The cells were maintained in DMEM (Gibco) at a glucose concentration of 4,500 mg/L and supplemented with 10% heat-inactivated fetal bovine serum (Gibco), 100 U/ml of penicillin and 100 $\mu$g/ml of streptomycin. Incubations were carried out at 37° C. in 95% air:5% $CO_2$. Cells grown in the above manner were washed and resuspended in DMEM (Gibco) containing 0.1% bovine serum albumin and 25 mM glucose. Cells were incubated with varying concentrations of insulinotropic peptides (i.e. glucagon, GLP-1 (1-37), GLP-1 (7-37), or GLP-1 (1-36 des-gly-arg amide); Peninsula Laboratories) for six hours, following which the effects of these agents on mRNA expression were determined. In all cases, the concentration of peptides was $10^{-7}$M. Incubations were for six hours.

Messenger RNAs specific for insulin, actin, or angiotensinogen were identified by Northern hybridization as follows: cellular RNA was extracted from solid tumors and cells by homogenization in guanidine thiocyanate and sedimentation through a cesium chloride cushion. Poly A+ RNA was isolated by oligo dT cellulose chromatography (Aviv, H., et al., Proc. Natl. Acad. Sci., USA 69:1408-1412 (1972)). Twenty micrograms of total RNA from each sample were fractionated by size on a 1.4% agarose gel after denaturation in glyoxal, followed by electrotransfer to a nylon membrane (Nytran; Schleicher and Schuell). Blotted membranes were baked for two hours at 80° C. under vacuum, prehybridized in 1M NaCl/1% SDS/10% Dextran sulfate at 50° C. overnight and hybridized at the same temperature for 24 h after addition of the labeled probes ($3-5 \times 10^5$ cpm/ml); they were then washed at 55° C. twice in 1$\times$SCC (0.15M NaCl/0.015M Na citrate)/1% SDS), and exposed to X-ray film for varying times at $-70°$ C. with an intensifying screen. The relative amounts of the specific mRNA were determined by microdensitometry. The results of this experiment are shown in Table 1.

The glucagon-like peptides increased the levels of insulin mRNA during 24-hr incubations (Table 1). The increase in insulin mRNA levels was consistently greater in response to the shorter, 31-amino acid peptide; 3-fold higher than control values at 24 hr. These stimulatory effects on insulin mRNA levels and on the release of insulin were observed in the presence of high (25 mM) and not low (5.5 mM) concentrations of glucose. Evidence that the stimulatory actions of GLP-1 are relatively specific for insulin mRNA was obtained by demonstrating that (i) GLP-1 (7-37) had negligible effects on levels of actin and angiotensinogen mRNAs in the insulinoma cell line; (ii) glucagon and GLP-II had no effects on insulin mRNA levels; and (iii) GLP-1 (7-37), when added to the rat islet glucagon-producing cell line 1056A and two pituitary cell lines, one producing prolactin (GH4) and the other corticotropin (AtT-20), had no effects on the levels of glucagon, prolactin, and corticotropin mRNAs, respectively.

GLP-1 (1-37) was examined to determine whether it could induce the biosynthesis of mRNA of hormones other than insulin. Thus, GLP-1 (1-37) (at a concentration of $10^{-7}$M) was added to a rat islet glucagon-producing cell line and two pituitary cell lines (GH4 and AtT-20) which were capable of producing the hormones prolactin and ACTH, respectively, and the amount of hormone specific mRNA produced was determined after 24 hours as described above. GLP-1 peptides had no detectable effect on either the level of prolactin mRNA in GH4 pituitary cells, or in the level of ACTH mRNA in AtT-20 pituitary cells.

TABLE 1

Densitometric quantitation of effects of glucagon-like peptides on levels of insulin and actin mRNAs in RIN 1046-38 cells

| mRNA | Peptide conc., M | Arbitrary densitometric units[1] | | | |
|---|---|---|---|---|---|
| | | Control[2] | GLP-1-(1-37) | GLP-1-(7-37) | GLP-1-(1-36)—NH$_2$ |
| | | Experiment 1 | | | |
| Insulin | $5 \times 10^{-7}$ | 1.28 ± 0.18 | 1.87 ± 0.35 | 4.23 ± 0.77[3] | 2.78 ± 0.51[4] |
| Actin | $5 \times 10^{-7}$ | 0.68 ± 0.03 | 0.48 ± 0.06 | 0.72 ± 0.16 | 0.87 ± 0.19 |
| Angiotensinogen | $5 \times 10^{-7}$ | 2.67 ± 0.31 | 2.25 ± 0.20 | 2.78 ± 0.46 | 2.56 ± 0.22 |
| | | Experiment 2 | | | |
| Insulin | $5 \times 10^{-11}$ | 5.90 (6.86, 4.99) | | 7.00 (5.58, 8.41) | |
| | $5 \times 10^{-10}$ | | | 6.70 (7.92, 5.50) | |
| | $5 \times 10^{-9}$ | | | 8.50 (7.59, 9.38) | |
| | $5 \times 10^{-8}$ | | | 7.90 (8.40, 7.40) | |
| Actin | $5 \times 10^{-11}$ | 2.69 (3.23, 2.15) | | 2.11 (1.86, 2.36) | |
| | $5 \times 10^{-10}$ | | | 2.09 (2.38, 1.79) | |
| | $5 \times 10^{-9}$ | | | 2.46 (2.01, 2.92) | |
| | $5 \times 10^{-8}$ | | | 1.99 (2.24, 1.74) | |
| | | Experiment 3 | | | |
| Insulin | $5 \times 10^{-7}$ | 5.56 ± 0.43 | | 13.87 ± 0.40[5] | |
| Actin | $5 \times 10^{-7}$ | 3.29 ± 0.08 | | 4.36 ± 0.44 | |

[1]Determined by scanning of autoradiograms of RNA blots. Values from experiments 1 and 3 are means ± SEM of triplicate plates of cells; values from experiment 2 are means of duplicates (individual values are given in parentheses). Statistical significance between control and experimental observations were calculated by Student's unpaired two-tailed t test.
[2]No peptide added.
[3]$P < 0.02$.
[4]$P < 0.05$.
[5]$P < 0.001$.

EXAMPLE 2 (Table 1)

The Effect of GLP-1 (7-37) on the Transcription of the Insulin and Other Genes

The effect of GLP-1 (7-37) on the transcription of the insulin and actin genes in RIN-38 insulinoma cells was investigated. Gene transcription rates were determined by quantification of nascent insulin and beta-actin RNA transcripts in nuclei from control and GLP 7-37 treated cells. The GLP-1 (7-37) concentration was $10^{-7}$M. Incubation was for 4 hours. Nuclear RNA was hybridized to an excess of cloned specific DNA bound to nitrocellulose and the filters were washed as described by McKnight, G. S., et al., (J. Biol. Chem. 254:9050-9058 (1979)). Rat insulin (Ullrich, A., et al., Science 196:113-119 (1977)) and, for control, chicken beta-actin cDNAs, provided by Dr. D. Cleveland, the Johns Hopkins University School of Medicine, Baltimore, Md., were used. Hybridization efficiency was controlled through the addition of the hybridization solution of [$^3$H] UTP insulin cRNA. Experiments were done in duplicate and values are expressed in ppm/kb of cDNA insert, corrected for efficiency of hybridization (40-50%). The results of this experiment revealed that GLP-1 (7-37) increased the rate of insulin gene transcription, but had no detectable effect upon the rate of actin gene transcription.

EXAMPLE 3

Effect of GLP-1 Derivatives on Cellular cAMP Levels

In order to determine whether glucagon-like proteins were capable of affecting cellular cAMP levels, the effects of GLP-1 (7-37) and GLP-1 (1-37) on cAMP levels in RINS-38 insulinoma cells (Expt. I and Expt. II, respectively) was determined.

Cells were grown as described in Example 1, in 26 well culture dishes. Varying amounts of glucagon-like peptides were added to culture wells in triplicate. After permitting incubation for 10 minutes, the total cell media was examined for cAMP, and the concentration of cAMP was determined. The results of this experiment are shown in Table 2. Twenty microliters from each culture well was assayed.

TABLE 2

| Peptide Concentration (M) | Expt. I | Expt II |
|---|---|---|
| 0 | 140 | 91 |
| $10^{-6}$ | 400 | 170 |
| $10^{-7}$ | 370 | 120 |
| $10^{-8}$ | 494 | 160 |
| $10^{-9}$ | 515 | 100 |
| $10^{-10}$ | 253 | 90 |
| $10^{-11}$ | 533 | 90 |

This experiment reveals that GLP-1 (7-37) was capable of stimulating cAMP levels even when present at a concentration of $10^{-11}$M. The increase in cAMP levels is an indication that GLP-1 (7-37) is capable of interacting with cellular receptors. In contrast, neither GLP-1 (1-37) nor GLP-II exhibited such activity.

A further experiment was performed in order to compare the insulinotropic activities of GLP-1 (1-37), GLP-1-(1-36)—NH$_2$ and GLP-1 (7-37) with the insulinotropic activity of glucagon. The procedures for this experiment are the same as those described above. The results of this experiment are shown in Table 3.

At the relatively high concentration of 0.5 μM, GLP-1 (1-37), GLP-1-(1-36)—NH$_2$, GLP-1 (7-37) and glucagon each increased cAMP levels. At 5 nM, GLP-1-(7-37) increased cAMP levels at least 4-fold and was still active at 50 pM. In contrast, the effects of glucagon, GLP-1-(1-37), and GLP-1-(1-36)—NH$_2$ on the formation of cAMP were negligible at these concentrations.

Figure 2:
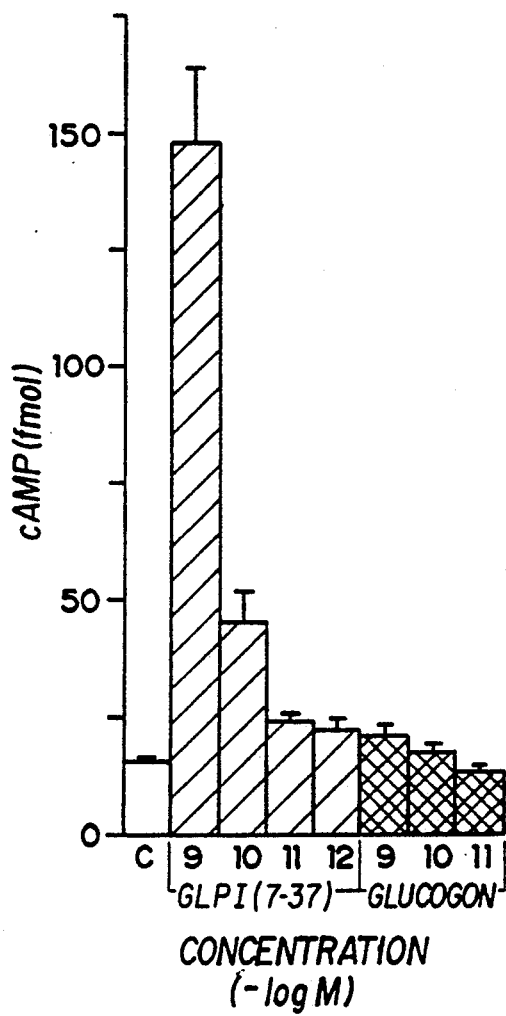
FIG. 2 shows the ability of the insulinotropic peptides glucagon and GLP-1 (7-37) to stimulate cAMP formation in the insulinoma line, RIN 1046-38.

The ability of the insulinotropic peptides glucagon and GLP-1 (7-37) to stimulate cAMP formation in the insulinoma line, RIN 1046-38, was investigated. Insulinotropic activity was monitored as described by Mojsov, S., et al., (J. Clin. Invest. 79:616-619 (1987)) and Drucker, D. J., et al., (Proc. Natl. Acad. Sci. 84:3434-3438 (1987)), both of which references are incorporated by reference herein. The results of this study are shown in FIG. 2, and indicate that GLP-1 (7-37) is at least 1000 times more potent than glucagon in inducing cAMP formation.

Again, samples 1 min apart were collected. The entire perfusion time was between 70 and 85 min.

In each aliquot of perfusate obtained, insulin was

TABLE 3

Stimulation of cAMP formation by glucagon and glucagon-like peptides in RIN 1046-38 cells

| Exp. | Peptide conc., M | No. of plates | cAMP, fmol* (mean ± SEM) | | | |
|---|---|---|---|---|---|---|
| | | | Control | GLP-1 (7-37) | Glucagon | GLP-1 (1-37) | GLP-1 (1-36)—NH$_2$ |
| 1 | No peptide | 8 | 15.4 ± 0.7* | | | |
| | 5 × 10$^{-12}$ | 5 | | 21.9 ± 2.0 (a) | 18.7 ± 2.2 (NS) | |
| | 5 × 10$^{-11}$ | 5 | | 23.9 ± 1.0 (c) | 13.2 ± 1.0 (NS) | |
| | 5 × 10$^{-10}$ | 5 | | 45.2 ± 5.9 (c) | 16.5 ± 2.0 (NS) | |
| | 5 × 10$^{-9}$ | 5 | | 148.0 ± 15.0 (c) | 20.1 ± 2.5 (a) | |
| 2 | No peptide | 4 | 43.6 ± 4.1 | | | |
| | 5 × 10$^{-8}$ | 4 | | 78.3 ± 3.4 (c) | 44.8 ± 1.6 (NS) | |
| | 5 × 10$^{-7}$ | 4 | | 83.0 ± 2.1 (c) | 93.1 ± 2.9 (c) | |
| 3 | No peptide | 5 | 34.4 ± 5.2 | | | |
| | 5 × 10$^{-10}$ | 5 | | 70.8 ± 5.2 (a) | | 27.6 ± 4.6 (NS) |
| | 5 × 10$^{-9}$ | 5 | | 134.0 ± 25.6 (b) | | 24.3 ± 1.9 (NS) |
| | 5 × 10$^{-8}$ | 5 | | 69.6 ± 7.0 (b) | | 30.8 ± 2.8 (NS) |
| | 5 × 10$^{-7}$ | 5 | | | | 69.9 ± 2.6 (c) |
| 4 | 5 × 10$^{-7}$ | 4 | 41.3 ± 7.1 | | | | 70.2 ± 2.8 (b) |

Statistical significance between control (no peptide) and experimental observations (by unpaired two-tailed t test) is as follows: a (P < 0.05); b (P < 0.01); c (P < 0.001); NS, not significant.
*All values are per 1/50th of cell extract per plate.

EXAMPLE 4

Effect of GLP-1 Peptides on Insulin Production

Rat insulinoma cells of cell line RIN-38 were grown in DME medium as described in Example 1. After incubation with 5×10$^{-7}$M GLP-1 (7-37), the concentrations of insulin in the cell culture mediums were determined by radioimmunoassay (as described above). Insulin protein levels were determined after incubation for 1 or 24 hours. The results of this experiment are shown in Table 4.

TABLE 4

| Peptide Added | Insulin Produced (μunits/ML) | |
|---|---|---|
| | 1 Hour | 24 Hours |
| None | 166 | 2,778 |
| GLP-7 (7-37) | 381 | 5,164 |

EXAMPLE 5

Pancreatic Perfusion Assay of Insulinotropic Activity

The pancreas of live rat was perfused with varying concentrations of GLP-1 (1-37) and GLP-1 (7-37) as described above. Isolated rat pancreas was prepared according to the method of Weir, G. C., et al., (J. Clin. Invest. 54:1403-1412 (1974)), and Penkos, J. C., et al. (Diabetes 18:733-738 (1969)). The perfusate contained bicarbonate buffer (pH 7.4) and 120 mg/dl glucose, 4% dextran T-70, and 0.2% bovine serum albumin, and was equilibrated with 95% oxygen and 5% carbon dioxide. The first 20 minutes of each perfusion was an equilibrium period. After this initial period, aliquots of perfusate were removed every 2-4 min for additional 20 min thus allowing the system to equilibrate for a total of 40 min. The perfusion, including any added insulinotropic peptide, was for 6 min and samples were collected at 1-min intervals. When more than one perfusion was to be performed, the peptide perfusions were followed by equilibration periods of 20 min, during which four samples 5 min apart were collected. A second 6-min perfusion followed with the same peptide as the first perfusion only at 100 times higher concentration of peptide.

determined by radioimmunoassay. In addition, the efficiency of delivery of the insulinotropic peptide was confirmed by radioimmunoassay of corresponding aliquots of perfusate in which insulin was measured (Mojsov, S. G., et al., J. Biol. Chem. 261:11880-11889 (1986), which reference is incorporated herein by reference). At one minute intervals, rat serum insulin levels in picograms/ml were determined by radioimmunoassay (as described above). The results of this experiment are shown in Table 5. Perfusions were done using peptide concentrations of 5×10$^{-7}$M, 5×10$^{-8}$M, and 5×10$^{-10}$M, 5×10$^{-11}$M, and 5×$^{-12}$M. Peptides were added after the zero minute serum value had been determined.

GLP-1 (1-37) was found to mediate a 3.4-fold increase in serum insulin concentrations when perfused into rat pancreas at a concentration of 5×10$^{-7}$M; at a concentration of 5×10$^{-8}$M, this peptide was capable of mediating only a two-fold increase in serum insulin levels. At a concentration of 5×10$^{-10}$M, this peptide was found to mediate only a 20% increase in serum insulin levels. The observed insulinotropic activity of GLP-1 (1-37) in these experiments most probably reflects the presence of GLP-1 (7-37) in the preparations (either through the degradation of GLP-1 (1-37) or due to low level contamination).

GLP-1 (7-37) was found to be capable of stimulating a 132-fold increase in insulin levels when provided to rat pancreas at a concentration of 5×10$^{-7}$M. At a 10-fold lower concentration (5×10$^{-8}$), this peptide was capable of directing a 21-fold increase in the serum concentration of insulin. At a concentration of 5×10$^{-10}$M, GLP-1 (7 -37) was found to be capable of mediating an increase in serum insulin levels (32-fold). Even at a concentration of 5×10$^{-11}$M, GLP-1 (7-37) delivered a 15-fold increase in insulin levels whereas GLP-1 (1-37) was without effect.

This experiment shows that GLP-1 (7-37) is more than 1,000-fold more potent than GLP-1 (1-37) in stimulating insulin expression in vivo. In addition, the GLP-1 peptides had no effects on the release of the peptide hormones glucagon and somatostatin in these same experiments. Thus, the stimulatory effects of GLP-1 are specific for the beta cells and do not act on pancreatic alpha or delta cells.

The level of GLP-1 (1-37) and GLP-1 (7-37) in rat portal blood has been measured by radioimmunoassay to be approximately 150 pg/ml (50 pM). The corresponding level in peripheral blood is 50 pg/ml (15 pM). The above-described results were obtained using GLP-1 (7-37) at a concentration of 5-50 pM. Thus, these results indicate that GLP-1 (7-37) has insulinotropic activity at its physiologic concentration.

TABLE 5

| | Insulin Produced (picograms/ml) at Peptide Concentration | | | | |
|---|---|---|---|---|---|
| Minutes | $5 \times 10^{-7}$M | $5 \times 10^{-8}$M | $5 \times 10^{-10}$M | $5 \times 10^{-11}$M | $5 \times 10^{-12}$M |
| GLP-1 (7-37) 0 | 50 | 925 | 205 | 160 | 50 |
| 1 | 6,600 | 20,700 | 7,400 | 2,400 | 50 |
| 2 | 4,700 | 10,500 | 1,800 | 1,700 | 50 |
| 3 | 1,700 | 4,000 | 760 | 1,900 | 98 |
| GLP-1 (1-37) 0 | 1,400 | 3,000 | 500 | 340 | 50 |
| 1 | 4,700 | 6,000 | 600 | 180 | 50 |
| 2 | 2,900 | 2,000 | 640 | 230 | 160 |
| 3 | 2,200 | 2,000 | 430 | 340 | 50 |

EXAMPLE 6

Comparison of the Insulinotropic Activities of Glucagon and GLP-1 (7-37)

Figure 3:
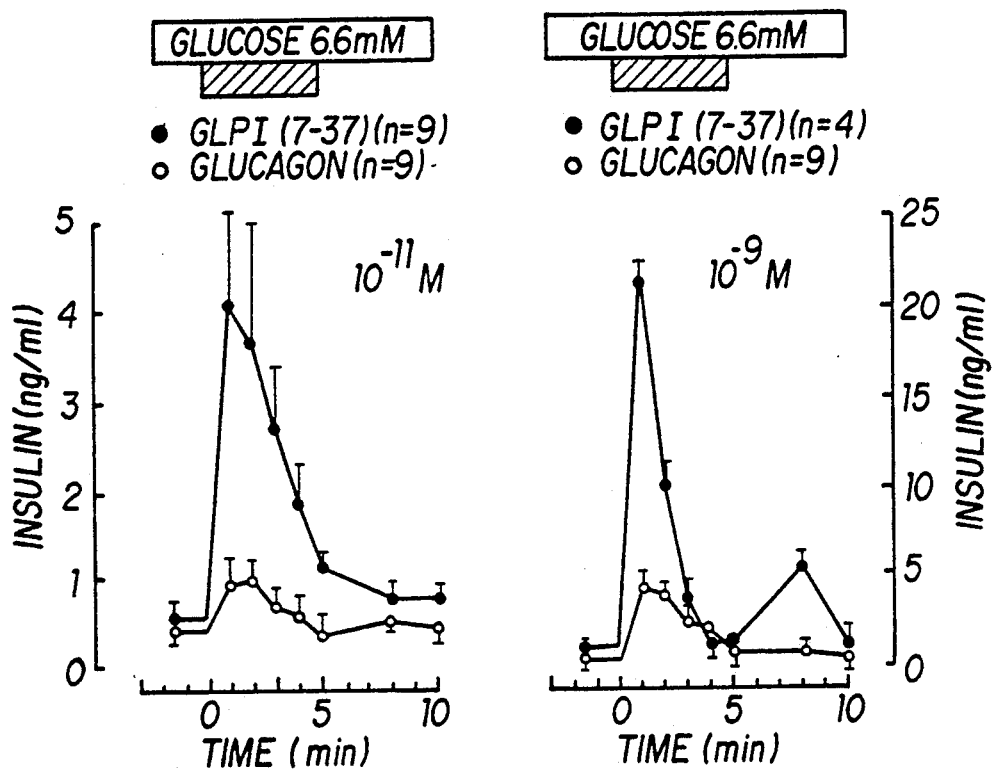
FIG. 3 shows a comparison of the insulinotropic activity of glucagon with that of GLP-1 (7-37).

Rat pancreas perfusion experiments were conducted as described in Example 5, in order to compare the insulinotropic activity of glucagon with that of GLP-1 (7-37). Peptides were perfused (for 5 minutes) at concentrations of $10^{-9}$M and $10^{-11}$M. As shown in FIG. 3, GLP-1 (7-37) was found to have more than 100 times the insulinotropic activity of glucagon.

This finding is confirmed by the study of the effects of glucagon, GLP-1 (1-37), and GLP-1 (7-37) on the cAMP levels in RIN 1046-38 insulinoma cells which is presented in Table 3.

relative insulinotropic activities. Insulinotropic activity was determined using the pancreatic perfusion assay of Example 6; the perfusion being carried out for 5 minutes. Peptides were present at a concentration of $10^{-11}$M. The results of this experiment are shown in Table 6. These results indicate that both GLP-1 (7-37) and GLP-1 (7-36)—NH$_2$ have substantial insulinotropic activity.

TABLE 6

| Comparison of the Insulinotropic Activity of GLP-1 (7-37) and GLP-1 (7-36)—NH$_2$ | | |
|---|---|---|
| Time (Minutes) | GLP-1 (7-36)—NH$_2$ | GLP-1 (7-37) |
| −1 | 985 ± 275 | 1330 ± 280 |
| +1 | 4550 ± 703 | 4200 ± 784 |
| +2 | 3330 ± 637 | 3280 ± 889 |
| +3 | 2500 ± 564 | 2500 ± 505 |

The effects of GLP-1 (7-37) and GLP-1 (7-36)—N$_2$ on cAMP formation in the insulinoma cell line RIN 1046-38 was determined using the procedure of Example 1. Cells were incubated for 10 minutes in the presence of 0, $10^{-11}$, $10^{-9}$, or $10^{-7}$M peptides. The results of this experiment are shown in Table 7. These results confirm that both GLP-1 (7-37) and GLP-1 (7-36)—NH$_2$ are insulinotropic peptides.

TABLE 7

EFFECTS OF GLP-1 (7-37) VERSUS GLP-1 (7-36)NH$_2$ ON cAMP FORMATION IN AN INSULINOMA CELL LINE (RIN 1046-38 CELLS).

| Peptide | N | IBMX (uM) | 0 | Peptide Concentration (M) | | |
|---|---|---|---|---|---|---|
| | | | | $10^{-11}$ | $10^{-9}$ | $10^{-7}$ |
| None (Control) | 8 | 100 | 161 ± 10* | | | |
| GLP-1 (7-37) | 4 | 100 | | 205 ± 9 | 202 ± 17 | 317 ± 65 |
| GLP-1 (7-36)NH$_2$ | 4 | 100 | | 141 ± 5 | 225 ± 16 | 358 ± 32 |
| None (Control) | 8 | 500 | 540 ± 22 | | | |
| GLP-1 (7-37) | 4 | 500 | | 501 ± 49 | 927 ± 75 | 2114 ± 421 |
| GLP-1 (7-36)NH$_2$ | 4 | 500 | | 446 ± 38 | 1199 ± 41 | 1676 ± 113 |

*All cAMP values are given as/fmoles/10 ul of cell extract

EXAMPLE 7

Insulinotropic Activity of Derivatives of GLP-1 (1-37)

Figure 4:
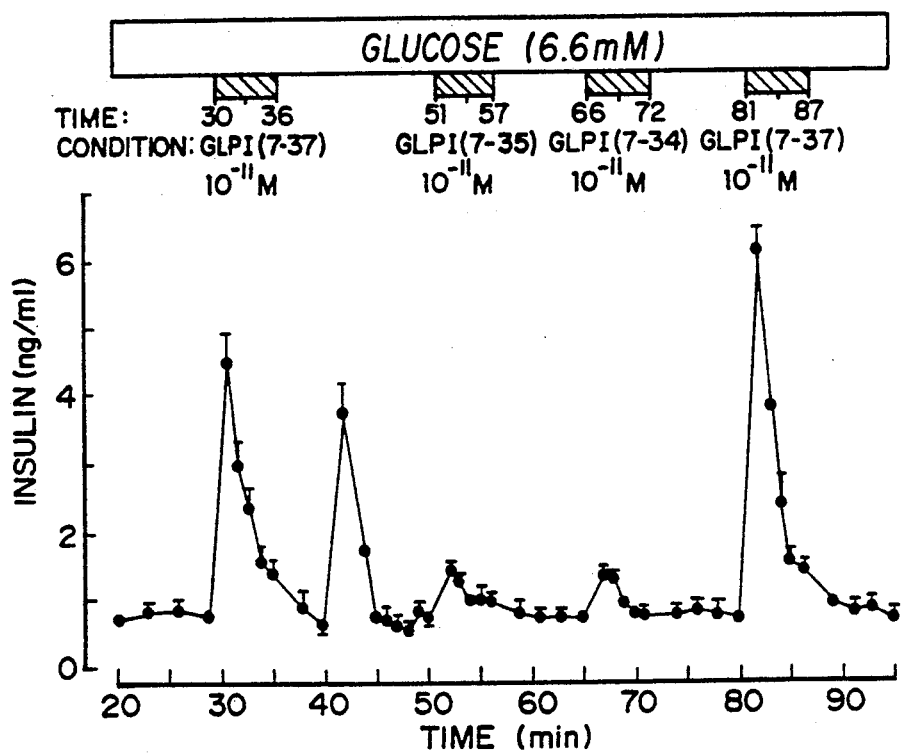
FIG. 4 shows a comparison of the insulinotropic activities of GLP-1 (7-34), GLP-1 (7-35), and GLP-1 (7-37) using the rat pancreas perfusion technique.

The insulinotropic activities of GLP-1 (7-34) and GLP-1 (7-35) were compared to that of GLP-1 (7-37) using the rat pancreas perfusion technique described above. Five minute perfusions were employed. As shown in FIG. 4 all three of these peptides had detectable insulinotropic activity at a concentration of $10^{-11}$M. These results indicate that the tested derivatives of GLP-1 (7-37) all have an insulinotropic activity greater than that of GLP-1 (1-37), which is inactive at $10^{-11}$M.

The GLP-1 related peptides: GLP-1 (7-36)—NH$_2$ and GLP-1 (7-37) were compared to determine their

EXAMPLE 8

Stability of GLP-1 (1-37)

Figure 5:
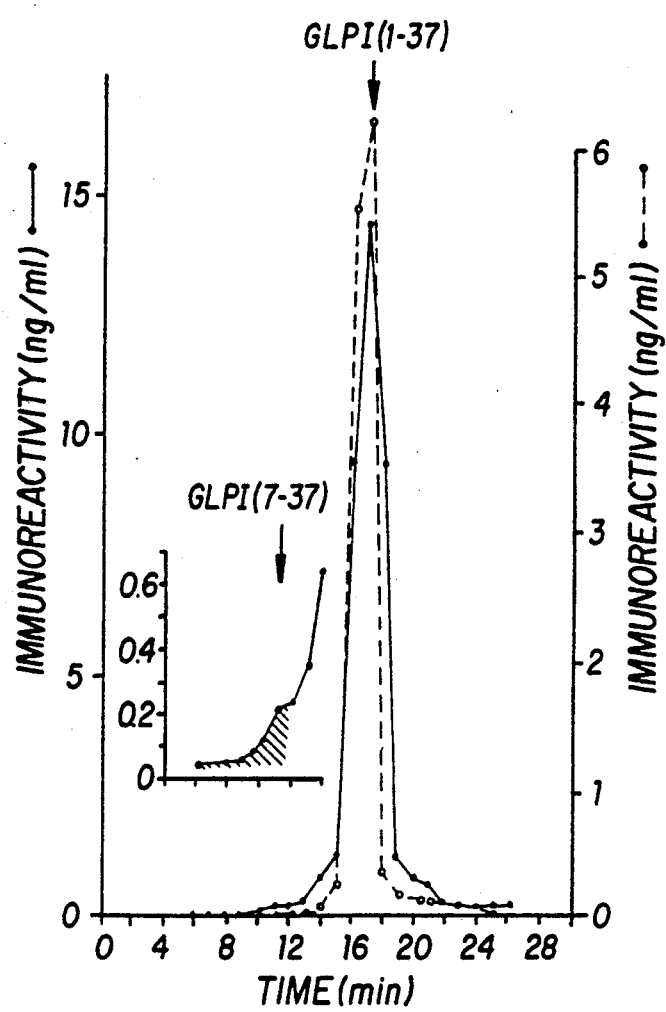
FIG. 5 shows the breakdown of GLP-1 (1-37) into GLP-1 (7-37) under experimental conditions.

To assess the stability of the 37 amino acid peptide in the experimental conditions, GLP-1 (1-37) was incubated for 24 hr in culture medium alone or in medium supplemented with either 0.1% bovine serum albumin or 10% fetal bovine serum. Aliquots of media were analyzed by high-pressure liquid chromatography and radioimmunoassay. Before incubation, no GLP-1 (7-37) was detected in the preparation of GLP-1 (1-37) (FIG. 5). However, after incubation of GLP-1 (1-37) in conditioned medium containing 0.1% bovine serum albumin, a small peak of GLP-1 (7-37) appeared, indicating that cleavage of GLP-1 (1-37) to the smaller, more active GLP-1 (7-37) occurs under these experimental conditions.

EXAMPLE 9

Insulinotropic Effect of GLP-1 (8-37)

As discussed above, glucagon has been found to be a beta-cell secretagogue, acting at concentrations as low as $10^{-9}$M. GLP-1 (7-37), which is co-encoded on the preproglucagon gene, has, as shown above, the capacity to mediate an insulinotropic effect even at concentrations as low as $10^{-12}$M. In order to determine if separate receptors might be involved in the recognition of glucagon and GLP-1 (7-37), a potential GLP-1 antagonist, the analog des-7 histidine GLP-1 (7-37) was constructed. This analog is hereinafter referred to "GLP-1 (8-37)".

Insulin secretion was studied in the perfused rat pancreas assay described above, with a perfusate glucose level of 6.6 mM. GLP-1 (8-37) was found to have no detectable effect at concentrations at $10^{-11}$, $10^{-9}$, or $10^{-8}$M. A weak insulinotropic activity was detected at $10^{-7}$M. At a perfusate glucose level of 16.7 mM the analog had no effect at $10^{-9}$M.

A similar experiment was conducted using glucagon. Glucagon was infused into rat pancreas for 5 minutes at a concentration of $10^{-9}$M with a perfusate glucose level of 6.6 mM, in either the presence or absence of $10^{-8}$M GLP-1 (8-37). Glucagon was found to elicit an elevated mean perfusate insulin concentration of 4.98±0.96 ng/ml, and virtually identical results (5.26±0.89 ng/ml) were seen with glucagon in the presence of GLP-1 (8-37) (N=4).

The above described protocol was used to study the effects of the GLP-1 (7-37) in the presence or absence of GLP-1 (8-37). GLP-1 (7-37), alone at a concentration of $10^{-11}$M stimulated mean insulin release of 2.25±0.30 ng/ml. This response was, however, lower (1.30±0.19 ng/ml (P<0.025, N=7 for each)) when the same dose was given on a background of the analog. These data indicate that the removal of the 7-histidine from GLP-1 (7-37) leads to a loss of agonist function in this system, and that agonist properties could be revealed. Because the agonist activity could only be demonstrated against GLP-1 (7-37), and not against glucagon, these two secretagogue appear to act through separate receptors.

Using the above-described perfused rat pancreas system, and a glucose perfusate of 6.6 mM, it was found that $10^{-9}$M GLP-1 (7-37) was capable of eliciting a biphasic pattern of insulin secretion with an initial spike of release followed by the plateau of sustained release. Furthermore, this response was found to be glucose-dependent; at $10^{-9}$M and a perfusate glucose concentration of 2.8 mM, no stimulation of insulin release was seen; at a perfusate glucose concentration of 6.6 mM or 16.7 mM, the mean incremental release above control was 4.7±1.0 or 22.8±4.7 ng/ml, respectively. GLP-1 (7-37) was found to be extraordinarily potent. At concentrations of $10^{-12}$M it was found to stimulate insulin secretion at a perfusate glucose concentration of 6.6 mM from a base line of 0.8±0.2 ng/ml to a peak of 1.6±0.5 ng/ml (P<0.05). When infused at $10^{-11}$M, insulin release was stimulated to a peak of 4.1±1.4 ng/ml and at $10^{-9}$M, a peak of 23.1±1.3 ng/ml was obtained. It is not yet known whether this GLP-1 peptide is secreted as the 7-37 form or is the 7-36-amide; both compounds were equally potent secretagogues.

Synthetic glucagon was far less potent with no release found at $10^{-11}$M. At $10^{-9}$M, however, glucagon was found to produce a peak of 4.5±0.5 ng/ml.

Thus, GLP-1 (7-37) and the 7-36-amide are candidates for physiological regulation as an "incretin" or as and endocrine modulator.

EXAMPLE 10

Affects of GLP-1 (8-37) on cAMP Formation in an Insulinomina Cell Line

A comparison of the insulinotropic effects of GLP-1 (8-37), GLP-1 (7-37) and glucagon on cAMP formation by the insulinoma cell line RIN 1046-38 was determined using the procedure of Example 1. The results of this experiment is shown in Table 8. These results show that GLP-1 (8-37) has an insulinotropic activity which is comparable to that of glucagon, and that GLP-1 (7-37) has an insulinotropic activity which is more than 100 times greater than that of either GLP-1 (8-37) or glucagon.

TABLE 8

Effects of GLP-1 (8-37) versus GLP-1 (7-37) and Glucagon on cAMP Formation in an Insulinoma Cell Line (RIN 1046-38 cells)

| Peptide | Concentration (M) | cAMP Formation* |
|---|---|---|
| None | | 27 ± 2 |
| GLP-1 (8-37) | $10^{-8}$ | 28 ± 0.8** |
| | $10^{-7}$ | 24 ± 2 |
| | $10^{-6}$ | 31 ± 3 |
| | $10^{-5}$ | 77 ± 11 |
| GLP-1 (7-37) | $10^{-8}$ | 128 ± 10 |
| Glucagon | $10^{-6}$ | 92 ± 9 |

*All cAMP levels are given as f-mole/5 ul of cell extract/15 min exposure to peptide
**Means ± S.E.M. (n = 4)

Having now fully described this invention, it will be apparent to one of ordinary skill in the art that the same may be carried out with minor modifications which do not affect the content or spirit thereof.

What is claimed is:

1. A molecule selected from the group consisting of:
(A) a peptide having the amino acid sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X
wherein X is selected from the group consisting of:
   (a) Lys, and
   (b) Lys-Gly;

and
(B) a derivative of said peptide (A), wherein said derivative is selected from the group consisting of:
   (1) a pharmaceutically acceptable acid addition salt of said peptide;
   (2) a pharmaceutically acceptable carboxylate salt of said peptide;
   (3) a pharmaceutically acceptable lower alkyl ester of said peptide; and,
   (4) a pharmaceutically acceptable amide of said peptide wherein said pharmaceutically acceptable amide is selected from the group consisting of amide, lower alkyl amide and lower dialkyl amide;

wherein said molecule is substantially free of natural contaminants, and has an insulinotropic activity which exceeds the insulinotropic activity of GLP-1 (1-36) or GLP-1 (1-37).

2. The molecule of claim 1 wherein X is Lys.
3. The molecule of claim 1 wherein X is Lys-Gly.

4. The molecule of claim 1 which is the peptide:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys.

5. The molecule of claim 1 which is the peptide:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly.

6. The molecule of claim 1 which is said derivative (B) of said peptide (A).

7. The molecule of claim 6, wherein said derivative (B) of said peptide (A) is selected from the group consisting of a lower alkyl amide and a lower dialkyl amide.

8. An insulinotropic composition which comprises an insulinotropic molecule in an amount effective for the treatment of maturity onset diabetes mellitus, said molecule being selected from the group consisting of:
  (A) a peptide having the amino acid sequence:
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X
  wherein X is selected from the group consisting of:
    (a) Lys, and
    (b) Lys-Gly;
and
  (B) a derivative of said peptide (A), wherein said derivative is selected from the group consisting of:
    (1) a pharmaceutically acceptable acid addition salt of said peptide;
    (2) a pharmaceutically acceptable carboxylate salt of said peptide;
    (3) a pharmaceutically acceptable lower alkyl ester of said peptide; and,
    (4) a pharmaceutically acceptable amide of said peptide wherein said pharmaceutically acceptable amide is selected from the group consisting of amide, lower alkyl amide and lower dialkyl amide;
wherein said molecule has an insulinotropic activity which exceeds the insulinotropic activity of GLP-1 (1-36) or GLP-1 (1-37); said molecule combined in admixture with a suitable pharmaceutically acceptable carrier.

9. The insulinotropic composition of claim 8, wherein X is Lys.

10. The insulinotropic composition of claim 8, wherein X is Lys-Gly.

11. The insulinotropic composition of claim 8, wherein said insulinotropic molecule is the peptide:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys.

12. The insulinotropic composition of claim 8, wherein said insulinotropic molecule is the peptide:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly.

13. The insulinotropic composition of claim 8, wherein said insulinotropic molecule is said derivative (B) of said peptide (A).

14. The insulinotropic composition of claim 13, wherein said derivative (B) of said peptide (A) is selected from the group consisting of a lower alkyl amide and a lower dialkyl amide.

15. A method for treating maturity onset diabetes mellitus in an individual in need of such treatment, said method comprising providing an amount of an insulinotropic molecule sufficient to treat said diabetes; wherein said molecule is selected from the group consisting of:
  (A) a peptide having the amino acid sequence:
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X
  wherein X is selected from the group consisting of:
    (a) Lys, and
    (b) Lys-Gly;
and
  (B) a derivative of said peptide (A), wherein said derivative is selected from the group consisting of:
    (1) a pharmaceutically acceptable acid addition salt of said peptide;
    (2) a pharmaceutically acceptable carboxylate salt of said peptide;
    (3) a pharmaceutically acceptable lower alkyl ester of said peptide; and,
    (4) a pharmaceutically acceptable amide of said peptide wherein said pharmaceutically acceptable amide is selected from the group consisting of amide, lower alkyl amide and lower dialkyl amide;
wherein said molecule has an insulinotropic activity which exceeds the insulinotropic activity of GLP-1 (1-36) or GLP-1 (1-37); said molecule combined in admixture with a suitable pharmaceutically acceptable carrier.

16. The method of treating maturity onset diabetes mellitus of claim 15, wherein X is Lys.

17. The method of treating maturity onset diabetes mellitus of claim 15, wherein X is Lys-Gly.

18. The method of treating maturity onset diabetes mellitus of claim 15, wherein said insulinotropic molecule is the peptide:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys.

19. The method of treating maturity onset diabetes mellitus of claim 15, wherein said insulinotropic molecule is the peptide:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly.

20. The method of treating maturity onset diabetes mellitus of claim 15, wherein said insulinotropic molecule is said derivative (B) of said peptide (A).

21. The method of treating maturity onset diabetes mellitus of claim 20, wherein said derivative (B) of said peptide (A) is selected from the group consisting of a lower alkyl amide and a lower dialkyl amide.

* * * * *

UNITED STATES PATENT AND TRADEMARK OFFICE
CERTIFICATE OF CORRECTION

PATENT NO. : 5,118,666
DATED : June 2, 1992
INVENTOR(S) : HABENER

It is certified that error appears in the above-indentified patent and that said Letters Patent is hereby corrected as shown below:

Column 1, line 26, delete "61=472-479" and insert therein --61:472-479--; line 28, delete "27=599-600" and insert therein --27:599-600--; line 31, delete "28=704-707" and insert therein --28:704-707--.

Page 1, Column 2, line 1, delete "302=716-718" and insert therein --302:716-718--; line 2, delete "260=3910-3914" and insert therein --260:3910-3914--.

UNITED STATES PATENT AND TRADEMARK OFFICE
CERTIFICATE OF CORRECTION

Page 2 of 6

PATENT NO. : 5,118,666
DATED : June 2, 1992
INVENTOR(S) : HABENER

It is certified that error appears in the above-indentified patent and that said Letters Patent is hereby corrected as shown below:

Please delete Figure 1:

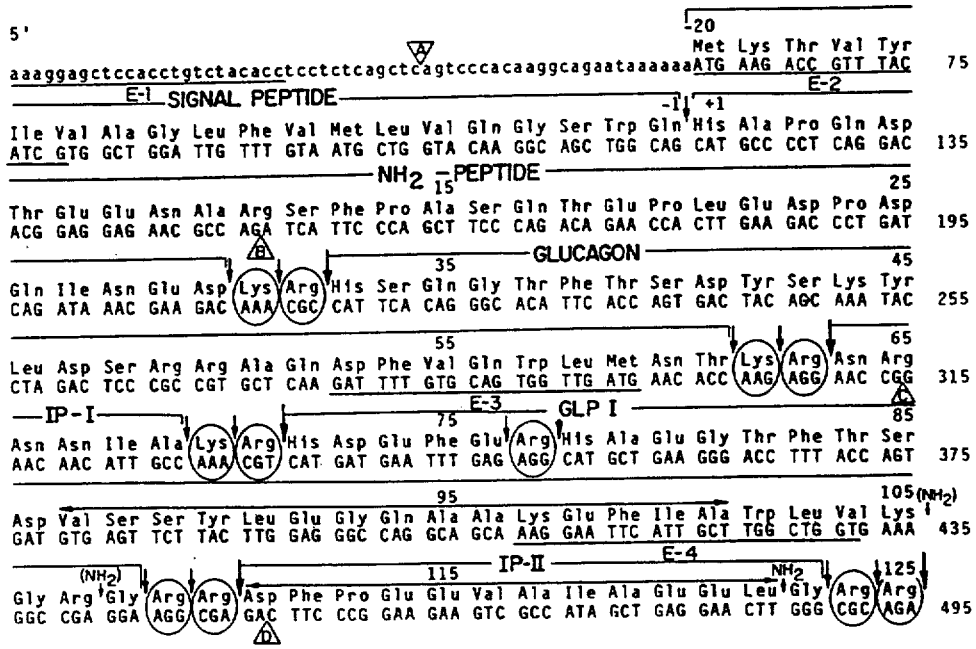

FIG. 1

UNITED STATES PATENT AND TRADEMARK OFFICE
CERTIFICATE OF CORRECTION

PATENT NO. : 5,118,666
DATED : June 2, 1992
INVENTOR(S) : HABENER

Page 3 of 6

It is certified that error appears in the above-indentified patent and that said Letters Patent is hereby corrected as shown below:

Figure 1 continued:

```
                              135 GLP II                                    145
His Ala Asp Gly Ser Phe Ser Asp Glu Met Asn Thr Ile Leu Asp Asn Leu Ala Thr Arg
CAT GCT GAT GGA TCC TTC TCT GAT GAG ATG AAC ACG ATT CTC GAT AAC CTT GCC ACC AGA   555
                      E-5            155
Asp Phe Ile Asn Trp Leu Ile Gln Thr Lys Ile Thr Asp (Lys)(Lys) End
GAC TTC ATC AAC TGG CTG ATT CAA ACC AAG ATC ACT GAC  AAG  AAA  TAG gaatatttcaccatt  618 cacaaccatcttcacaacatctcctgccagtcacttgggatgtacatttgagagcatatccgaagctatactgctttgc   697
              E-6
atgcggacgaatacatttccctttagcgttgtgtaacccaaaggttgtaaatggaataaagttttccagggtgttgat   776 aaagtaacaactttacagtatgaaaatgctggattctcaaattgtctcctcgttttgaagttaccgccctgagattact   855 tttctgtggtataaattgtaaattatcgcagtcacgacacctggattacaacaacagaagacatggtaacctggtaacc   933 gtagtggtgaacctggaaagagaacttcttccttgaacccttttgtcataaatgcgctcagctttcaatgtatcaagaat 1012 agatttaaataaatatctcat                                                           1024
          3'
```

*FIG. 1 CONT.*

UNITED STATES PATENT AND TRADEMARK OFFICE
CERTIFICATE OF CORRECTION

PATENT NO. : 5,118,666
DATED : June 2, 1992
INVENTOR(S) : HABENER

It is certified that error appears in the above-indentified patent and that said Letters Patent is hereby corrected as shown below:

And replace therein corrected Figure 1:

```
5'                                                           -20
                                                             Met Lys Thr Val Tyr
aaaggagctccacctgtctacacctcctctcagctcagtcccacaaggcagaataaaaaaATG AAG ACC GTT TAC  75
——————————— SIGNAL PEPTIDE ——————————
                                                         -1  +1
Ile Val Ala Gly Leu Phe Val Met Leu Val Gln Gly Ser Trp Gln His Ala Pro Gln Asp
ATC GTG GCT GGA TTG TTT GTA ATG CTG GTA CAA GGC AGC TGG CAG CAT GCC CCT CAG GAC 135
———————————————— NH2-PEPTIDE ————————————————
                           15                                                25
Thr Glu Glu Asn Ala Arg Ser Phe Pro Ala Ser Gln Thr Glu Pro Leu Glu Asp Pro Asp
ACG GAG GAG AAC GCC AGA TCA TTC CCA GCT TCC CAG ACA GAA CCA CTT GAA GAC CCT GAT 195
                                    35 ———————— GLUCAGON ————————— 45
Gln Ile Asn Glu Asp (Lys)(Arg) His Ser Gln Gly Thr Phe Thr Ser Asp Tyr Ser Lys Tyr
CAG ATA AAC GAA GAC (AAA)(CGG) CAT TCA CAG GGC ACA TTC ACC AGT GAC TAC AGC AAA TAC 255
                                55                                         65
Leu Asp Ser Arg Arg Ala Gln Asp Phe Val Gln Trp Leu Met Asn Thr (Lys)(Arg) Asn Arg
CTA GAC TCC CGC CGT GCT CAA GAT TTT GTG CAG TGG TTG ATG AAC ACC (AAG)(AGG) AAC CGG 315
—IP-I—                      75 ————————— GLP I ———————————— 85
Asn Asn Ile Ala (Lys)(Arg) His Asp Glu Phe Glu Arg His Ala Glu Gly Thr Phe Thr Ser
AAC AAC ATT GCC (AAA)(CGT) CAT GAT GAA TTT GAG AGG CAT GCT GAA GGG ACC TTT ACC AGT 375
                              95                                       105
Asp Val Ser Ser Tyr Leu Glu Gly Gln Ala Ala Lys Glu Phe Ile Ala Trp Leu Val Lys
GAT GTG AGT TCT TAC TTG GAG GGC CAG GCA GCA AAG GAA TTC ATT GCT TGG CTG GTG AAA 435
——————————————— IP-II ——————————————
                    115                                         125
Gly Arg Gly (Arg)(Arg) Asp Phe Pro Glu Glu Val Ala Ile Ala Glu Glu Leu Gly (Arg)(Arg)
GGC CGA GGA (AGG)(CGA) GAC TTC CCG GAA GAA GTC GCC ATA GCT GAG GAA CTT GGG (CGC)(AGA) 495
```

Page 4 of 6

UNITED STATES PATENT AND TRADEMARK OFFICE
CERTIFICATE OF CORRECTION

Page 5 of 6

PATENT NO. : 5,118,666
DATED : June 2, 1992
INVENTOR(S) : HABENER

It is certified that error appears in the above-indentified patent and that said Letters Patent is hereby corrected as shown below:

```
                              ————— GLP II —————
                                 135                                    145
His Ala Asp Gly Ser Phe Ser Asp Glu Met Asn Thr Ile Leu Asp Asn Leu Ala Thr Arg
CAT GCT GAT GGA TCC TTC TCT GAT GAG ATG AAC ACG ATT CTC GAT AAC CTT GCC ACC AGA  555

155
Asp Phe Ile Asn Trp Leu Ile Gln Thr Lys Ile Thr Asp (Lys)(Lys) End
GAC TTC ATC AAC TGG CTG ATT CAA ACC AAG ATC ACT GAC (AAG)(AAA) TAG gaatatttcaccatt  618 cacaaccatcttcacaacatctcctgocagtcacttgggatgtacatttgagagcatatccgaagctatactgctttgc  697
atgcggacgaatacatttccctttagcgttgtgtaacccaaaggttgtaaatggaataaagtttttccagggtgttgat  776
aaagtaacaactttacagtatgaaaatgctggattctcaaattgtctcctcgttttgaagttaccgccctgagattact  855
tttctgtggtataaattgtaaattatcgcagtcacgacacctggattacaacaacagaagaoatggtaacctggtaacc  933
gtagtggtgaacctggaaagagaacttcttccttgaacccttttgtcataaatgcgctcagctttcaatgtatcaagaat  1012
agatttaaataaatatctcat                                                          1024
                    3'
```

UNITED STATES PATENT AND TRADEMARK OFFICE
CERTIFICATE OF CORRECTION

PATENT NO. : 5,118,666
DATED : June 2, 1992
INVENTOR(S) : HABENER

It is certified that error appears in the above-indentified patent and that said Letters Patent is hereby corrected as shown below:

Column 4, line 30, delete "previosly" and insert therein --previously--; line 54, delete "*et a.,*" and insert therein --*et al.*,--.

Column 5, line 1, delete "well-know" and insert therein --well-known--.

Column 6, line 53, between "of" and "insulin" insert --[$^{125}$I]--.

Column 9, line 34, delete "sectretion" and insert therein --secretion--; line 50, delete "intented" and insert therein --intended--.

Column 11, line 28, delete "(Table 1)."; line 54, insert --(Table 1)-- after "transcription."

Column 18, line 6, delete "and" and insert therein --an--; line 10, delete "Insulinomina" and insert therein --Insulinoma--.

Signed and Sealed this

Twelfth Day of December, 1995

Attest:

*Attesting Officer*

BRUCE LEHMAN

*Commissioner of Patents and Trademarks*

UNITED STATES PATENT AND TRADEMARK OFFICE
Certificate

Patent No. 5,118,666                                                                                                 Patented: June 2, 1992

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Joel Habener, Newton Highlands, MA; and Svetlana Mojsov, New York, NY.

Signed and Sealed this Sixteenth Day of November 2004.

CHRISTINA CHAN
*Supervisory Patent Examiner*
Art Unit 1644